(12) United States Patent
Abraham

(10) Patent No.: US 6,450,639 B1
(45) Date of Patent: Sep. 17, 2002

(54) FOG-FREE PROTECTIVE GLASSES, GOGGLES, AND NON-PROTECTIVE GLASSES

(76) Inventor: Carl J. Abraham, 3 Baker Hill Rd., Great Neck, NY (US) 11023

(*) Notice: Subject to any disclaimer, the term of this patent is extended or adjusted under 35 U.S.C. 154(b) by 0 days.

(21) Appl. No.: 09/872,459

(22) Filed: Jun. 2, 2001

(51) Int. Cl.$^7$ .............................. G02C 11/08
(52) U.S. Cl. .................. 351/62; 351/41; 2/435
(58) Field of Search .................. 351/62, 41, 44; 2/435

(56) References Cited

U.S. PATENT DOCUMENTS

| | | | |
|---|---|---|---|
| 1,354,433 A | * | 9/1920 | De-Felice .............. 351/62 |
| 4,011,595 A | | 3/1977 | Shields |
| 4,150,443 A | | 4/1979 | McNeilly |
| 4,707,863 A | | 11/1987 | McNeal |
| 5,018,223 A | | 5/1991 | Dawson |
| 5,459,533 A | | 10/1995 | McCooeye |
| 5,610,668 A | | 3/1997 | Mage |
| 5,652,965 A | | 8/1997 | Crooks |
| 5,898,468 A | | 4/1999 | Mage |
| 6,065,833 A | | 5/2000 | Tiano |
| 6,119,276 A | | 9/2000 | Newcomb |

* cited by examiner

Primary Examiner—Hung Xuan Dang

(57) ABSTRACT

Improved eyewear designs allow for circulation of air between the eyes and lenses to prevent fog from appearing on the lenses, the eyewear utilized in a host of sporting activities and work areas that require glasses or goggles for safety purposes. A first embodiment of the invention teaches the use of beveled members affixed to the interior portion of the frames of the glasses or goggles, such that the spaced apart members come in direct contact with the user's forehead, allowing for continuous air flow between the beveled members to the user's eyes. The spacers may be placed on the inside of the frames, attached to the frames by simple adhesives. The distance between the spacers may be of a range of one-quarter to three-eighths inches, and the spacers may be of a similar width as the outside frame. The edges may be rounded or beveled for user comfort. Regarding goggles that completely enclose the eye area, an additional embodiment describes eyewear frames bearing air holes through the circumference of each eye portion. The size of such apertures may range from one-sixteenth to three-eighths inches in diameter, and are included to accomplish the purpose of allowing sufficient airflow through the eye area to prevent fog from forming.

15 Claims, 3 Drawing Sheets

FOG-FREE PROTECTIVE GLASSES, GOGGLES, AND NON-PROTECTIVE GLASSES

BACKGROUND OF THE INVENTION

1. Field of the Invention

The present invention relates to eyewear designs that allow for circulation of air between the eyes and lenses. Such is for the purpose of preventing fog from appearing on the lenses—a consistent problem in a host of sporting activities and work areas that require glasses or goggles for safety purposes. Such is uncomfortable and often dangerous for the user.

A first embodiment of the present invention teaches the use of beveled members affixed to the interior portion of the frames of the glasses or goggles, such that the spaced apart members come in direct contact with the user's forehead. This design allows for continuous air flow between the beveled members to the user's eyes, while still protecting the eyes from direct impact from objects.

Furthermore, spacers may be placed on the inside of the frames, attached to the frames by simple adhesives. The distance between the spacers may be of a range of one-quarter to three-eighths inches, and the spacers may be of a similar width as the outside frame. Importantly, the edges may be rounded or beveled for the purposes of user comfort.

Finally, regarding goggles that completely enclose the eye area, an additional embodiment of the present invention teaches the usage of eyewear frames bearing air holes through the circumference of each eye portion. The size of such apertures may range from one-sixteenth to three-eighths inches in diameter, and are included to accomplish the purpose of allowing sufficient airflow through the eye area to prevent fog from forming upon the goggles.

In total, the designs of the present invention mitigate or prevent undesired fog from forming upon protective or non-protective eyewear in an effective manner that does not add to the manufacturing cost of the products. Importantly, the protection provided by the eyewear and the appearance of the products are not in any way compromised by the present invention.

2. Description of the Prior Art

Numerous innovations for fog-reducing eyewear devices have been provided in the prior art that are described as follows. Even though these innovations may be suitable for the specific individual purposes to which they address, they differ from the present invention as hereinafter contrasted. The following is a summary of those prior art patents most relevant to the invention at hand, as well a description outlining the differences between the features of the present invention and those of the prior art.

1. U.S. Pat. No. 5,610,668, invented by Mage, entitled "Fog-Resistant Sunglasses Incorporating Ventilation Channels"

The patent to Mage describes protective eyeglasses (e.g., sunglasses) for use in high-speed outdoor sports activities, the lenses thereof being resistant to condensation, achieved by air circulation created by venturi effects. The glasses comprise a frame front having middle portions over the wearer's eyes which support protective lenses, and having endpiece portions near the wearer's temples, the outboard edges of which attach temples which hold the glasses in place. A chamber is defined by the volume between the lenses and the wearer's face, and gaps are defined by the distance between the middle portions of the frame front and the wearer's face. Apertures in each of the endpiece portions of the frame front define an entrance of a ventilation channel for air flow through the frame front, adjacent to the respective chamber. Venturi forces are created within the ventilation channels to facilitate circulation of air. Improved ventilation, and the reduction or elimination of fogging on the lenses, is accomplished by low-cost and lightweight glasses.

2. U.S. Pat. No. 5,898,468, invented by Mage, entitled "Fog-Resistant Sunglasses Incorporating Ventilation Channels Fog-Resistant Sunglasses Incorporating Ventilation Channels"

This patent to Mage describes protective eyeglasses resistant to fogging while being worn by a wearer. The eyeglasses comprise a frame front which spans across the wearer's face and includes a forward side, an aft side, at least one middle portion extending over the wearer's eyes, and a pair of end piece portions near the wearer's temples. Attached to the middle portion of the frame front is at least one lens which is positioned over the wearer's eyes and defines front and back surfaces. Additionally, disposed within the frame front is at least one forwardly directed aperture which defines a ventilation channel for facilitating airflow through the frame front adjacent the lens. The ventilation channel defined by the aperture is sized and configured to facilitate the circulation of air over the back surface of the lens to resist the fogging thereof.

3. U.S. Pat. No. 4,011,595, invented by Shields, entitled "Defoggable Goggles"

The patent to Shields describes goggles having a wide lens mounted in a semi-rigid frame which positions the lens away from the face providing an enclosed air space, the frame having a number of apertures permitting an influx of air, and one or more outlet apertures to which are secured means for evacuating air from the inner space. The evacuating means takes the form of a conduit which can be placed in the wearer's mouth to draw air out of the inner space.

4. U.S. Pat. No. 5,018,223, invented by Dawson et al., entitled "Non-Fogging Goggles"

The patent to Dawson et al. describes non-fogging goggles which include a double lens that consists of a pair of two spaced-apart lenses that have an air interstice therebetween and in which the inner surface of the outer lens is coated with a metal film. The metal coating is preferably made of gold and is vacuum-deposited on the outer lens. The body heat radiated by the user is reflected on the metal film and reduces the temperature differential between the inner lens and the area enclosed by the goggles, thereby preventing fogging of the inner lens. The radiated heat will also contribute in maintaining the temperature of the lens of any corrective eyeglasses worn under the goggles.

5. U.S. Pat. No. 4,150,443, invented by McNeilly, entitled "Anti-Fogging Sports Goggle"

The patent to McNeilly describes a sports goggle provided with power means in the form of a miniature electrical fan mounted within the air space defined by the goggle and the face of the wearer when the goggle is in place. The fan is selectively actuatable by the wearer of the goggle to draw the warm humid air within the air space into the fan, to compress the same therein, and to circulate the same throughout the air space to prevent condensation build-up on the inner surface of the lens structure of the goggle and on eyeglasses of the wearer of the goggle. The fan also urges the circulated warm humid air outwardly of the goggle through air passages provided in the shell of the goggle so that ambient air may enter the goggle to replace the forced out air without admitting snow or other precipitation from the ambient.

6. U.S. Pat. No. 6,065,833, invented by Tiano, entitled "Sporting Eyeglasses"

The patent to Tiano describes sportsman's eye wear designed to overcome the difficulties and problems associated with conventional eye wear designs. The sporting eyeglasses are specially designed to afford the serious hunter, fisherman or outdoorsman superior eye protection in a stylish manner while providing a effective means by which to secure them to the user's head and maintain their position. The eyeglasses also include anti-fogging ventilation, a camouflaging veil and allow for the incorporation of prescription lenses.

7. U.S. Pat. No. 5,459,533, invented by McCooeye et al., entitled "Defogging Eye Wear"

The patent to McCooeye et al. describes an eye wear device comprising a frame and lens means supported by the frame to be positioned in front of a wearer's eyes. The improvement characterized in that the lens means is coated with an electrically conductive heat generating layer to be positioned in the wearer's field of vision when the eye wear is worn, and of sufficient resistance to produce enough heat to remove moisture build-up on the lens means. Contacts are provided at either end of the layer, each contact electrically associated with the layer, an electronic moisture sensor means associated with the lens means to detect a moisture build-up on the lens means, circuitry associated with the contacts and moisture sensor, in operation to be electrically connected to a power source, microchip means electrically associated with the circuitry and moisture sensor, and arranged to permit a flow of current from the power source across the layer when moisture builds up on the lens to a predetermined degree, and to stop that flow of current across the layer when the moisture level on the lens falls below a predetermined degree.

8. U.S. Pat. No. 6,119,276, invented by Newcomb et al., entitled "Sport Goggle"

In the patent to Newcomb, a sport goggle and system for ventilating a sport goggle is described. The goggle has a strap, lens structure, and frame having a first edge extending laterally across the forehead. The first edge is shaped such that a portion of same is curved in a concave up direction when the goggle is in use, and such that when the goggle is worn with a helmet, one or more gaps are created between the first edge and second edge on the front of the helmet. The first edge has a first opening to allow air to flow into the goggle chamber. Increased ventilation through the opening can be caused by either the concave up portion, or the gaps between the first and second edges.

9. U.S. Pat. No. 5,652,965, invented by Crooks, entitled "Non-Fogging Goggles"

In the patent to Crooks, non fogging goggles are disclosed. An air scoop is provided at the bottom side of the goggles providing an air port with a cross sectional area of at least 1 square inch open in the front side of said frame for permitting air to enter the goggles. When the user is facing into a head wind, which may be self created, air is forced into the-goggles so as to cause a positive air pressure. A valve located at the top side of the goggle controls the amount of air passing through the goggles. In a preferred embodiment the valve comprises a spacer with four square ports ½ inch on a side, two ports on each side. One port on each side is covered with very light foam screen. The other two ports are unrestricted. A slider contains two ½ inch square ports which can be aligned by the wearer over the screened ports in the spacer or the unrestricted ports. The screened ports are utilized while in motion or during driving snow storms. The unrestricted ports are utilized while motionless on windless days while standing in lift lines.

10. U.S. Pat. No. 4,707,863, invented by McNeal, entitled "Anti-Fog Goggle With Foam Frame"

In the patent to McNeal, an anti-fog goggle is provided having a foam frame with a method of manufacturing the goggle. The goggle is composed of generally planar individual members, yet the goggle has a desired degree of self-supporting curvature. The anti-fog goggle has a semi-rigid support member for supporting the goggle's lens, the support member being stamped out of a planar sheet of foam. The foam support member has air channels depressed therein through which air enters and exits the interior of the goggle to prevent condensation from forming on the viewing surface of the lens' interior. The lens is stamped from a planar sheet of transparent plastic which is deformable into a simple curve. The lens is formed with a plurality of apertures therein which are aligned with air channels in the support member when the lends is secured thereto. The lens' apertures form ports through which air may flow into the air channels, the air channels directing the air downward across the inner surface of the lens. To make the goggle, the support member is curved about a form having the generally desired curvature and the lens adhered to the curved support member with an adhesive to deform the lens and support member into the form curvature which is substantially maintained when the lens and support member are removed from the form. The goggle may also include a cushioning foam member which is adhered to the inner surface of the semi-rigid foam support member to cushion contact with the wearer's face.

The aforementioned prior art patents illustrate various designs intended to prevent fog upon glasses or goggles. For example, the patents to Mage (first and second above-listed) show apertures within glasses frames for air circulation. However, the eyewear is intended for "high-speed sport activities" and such holes are on the sides and center of the frames only—not around the perimeter of the frames. Moreover, the patent to Tiano shows apertures within goggle frames for air circulation. However, such holes are "linearly disposed along said upper edge of said frame" only—not around the perimeter of the frames.

Other relevant prior art designs include: a conduit or mouth tube for drawing air from the goggle chamber (patent to Shields); goggles with a power means or electrical fan for de-fogging (patents to McNeilly, McCooeye); and goggles with a valve means to regulate the flow of air into the goggle chamber when the user travels into a head wind (patent to Crooks).

In contrast to the above, the present invention may include spaced apart or beveled members on the interior portion of the frames, to come in direct contact with the forehead and allow air flow between the eyes and lenses. The distance between spacers may be one-quarter to three-eighths inches, and the spacers may be of a similar width as the outside frame. The edges may be rounded for user comfort.

Alternatively, the present invention may include air holes throughout the circumference of each eye portion of fully-enclosed goggles. The apertures may range from one-sixteenth to three-eighths inches in diameter, to allow sufficient airflow to prevent fog from forming. Such designs do not add significantly to the cost of the product, and the appearance and safety of the product is maintained.

SUMMARY OF THE INVENTION

There is presently, and there has been a consistent problem regarding the fogging of lenses of eyewear, such as protective glasses, goggles, and non-protective glasses. The fog forms as a result of the differential in temperature between the outside air and the area just in front of and above the user's nose and eyes, particularly when the user is engaging in a sporting activity that causes perspiration. Such fogging of lenses commonly occurs in sports such as tennis, racquetball, hockey, and cycling, much to the detriment of the athlete or user.

At the root of the problem is the fact that present designs do not allow for sufficient circulation of air between the eyes and lenses. Thus, a need exists for a product that allows air to enter the user's eye area in such a manner as to prevent or mitigate fogging. As noted, relevant prior art devices typically teach the usage of chemically treated wipes that are applied directly to the lenses, or devices that allow air to enter glasses or goggles only from the top thereof. Thus, the prior designs are either temporary in nature or generally insufficient.

The present invention, in contrast, is a permanent solution that is designed directly into the glasses or goggles themselves. Importantly, the safety and protection afforded by the device are not altered or compromised in any way, the appearance of the item is not diminished, and the improved device is relatively inexpensive to manufacture.

The primary modification to the glasses or goggles is made in the frame of the eyewear. In a first embodiment, the present invention teaches the use of multiple beveled members affixed to the interior portion of the frames, such that the spaced-apart members come in direct contact with the user's forehead. Due to their moving of the lenses away from the user's face, this design allows for continuous air flow between the spacer members to the user's eyes, while still protecting the eyes from direct impact from other persons or objects.

Furthermore, the spacer members may be conveniently placed on the inside of the frames, removably attached to the frames by simple adhesives. In the preferred mode, the distance between the spacer members is of a range of one-quarter to three-eighths inches, and the spacer members may be of a similar width as the outside frame of the glasses or goggles. Importantly, the spacer member edges may be rounded or beveled for the purpose of user comfort.

Regarding eyewear that completely encloses the eye area, a second embodiment of the present invention teaches the usage of frames bearing air holes through and around the periphery of each eye portion. The size of such apertures may range from one-sixteenth to three-eighths inches in diameter, and such apertures also accomplish the purpose of allowing sufficient airflow to the user's eye and nose area to prevent fog from forming.

In summation, in light of the foregoing, it is an object of the present invention to provide eyewear items that are resistant to the formation of fog, allowing the user's full vision to remain intact.

It is a further object of the invention to provide an apparatus that still effectively protects the eye area of the user from injury caused by impact from persons or flying objects.

It is a further object of the present invention to provide a device that is relatively inexpensive to manufacture and produce.

In addition, it is an object of the present invention to provide a fog-prevention assembly that may be easily retrofitted to previously existing protective glasses, goggles, and non-protective glasses.

Finally, it is an object of the present invention to provide alternate embodiments that each effectively mitigate the incidence of fog forming upon eyewear, much to the benefit of the user.

The novel features which are considered characteristic for the invention are set forth in the claims. The invention itself, both as to its construction and its method of operation, together with additional objects and advantages thereof, will be best understood from the following description of the embodiments when read and understood in connection with accompanying drawings.

BRIEF DESCRIPTION OF PREFERRED EMBODIMENTS

DETAILED DESCRIPTION OF THE PREFERRED EMBODIMENT

Figure 1:
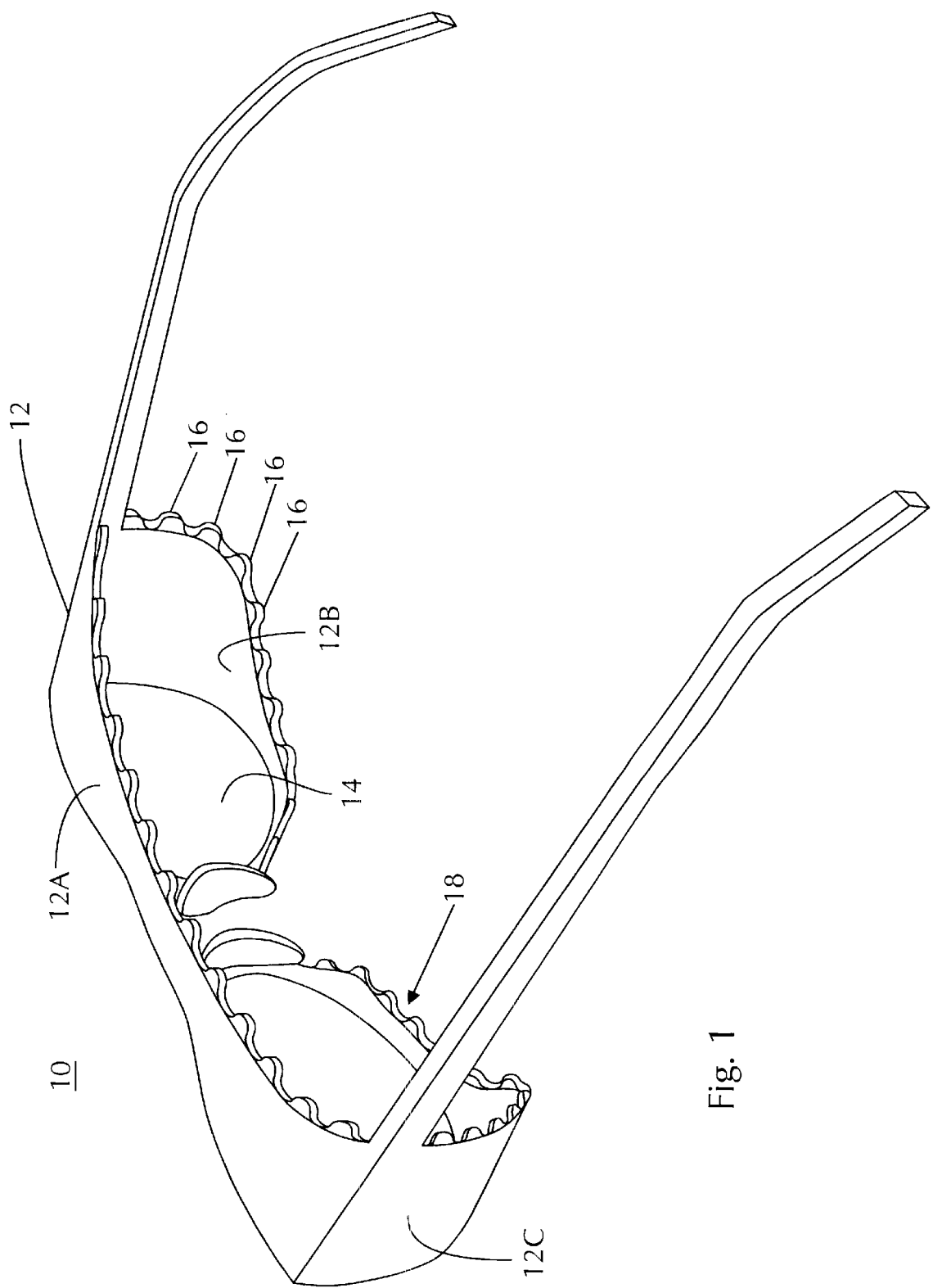
FIG. 1 is a front, three-quarter perspective view of a first embodiment of the present invention, illustrating the principal components utilized to mitigate formation of fog.
Figure 1A:
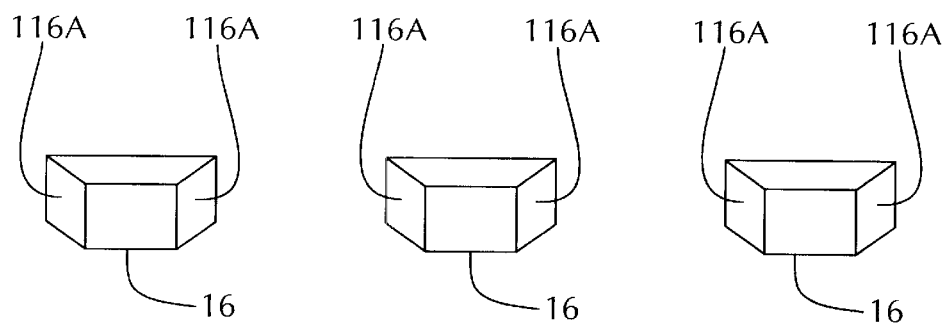
FIG. 1A is a front perspective view of several spacer members of the embodiment of the present invention illustrated in FIG. 1.

Referring to FIG. 1, which is a front, three-quarter perspective view of a first embodiment of the present invention, illustrating the principal components utilized to mitigate formation of fog; and FIG. 1A, which is a front perspective view of several spacer members of the embodiment of the present invention illustrated in FIG. 1:

For the purposes of example only, such figures depict an eyewear frame (12), frame top portion (12A), frame bottom portion (12B), frame side portion (12C), lens (14), spacer members (16), and cavity between spacer members (18). Furthermore, illustrated in FIG. 1A are spacer members (16), comprising spacer member side portions (16A). The frame (12) may be of any number of previously-existing styles, such as conventional goggles that completely enclose the eye area, goggles or visors that come in contact with only the user's forehead, or protective or non-protective glasses, which are all susceptible to condensation buildup and fog during ordinary usage.

As previously noted, the lens (14) of any embodiment of the present invention need not be altered in any manner, as the invention does not need the usage of chemically-treated wipes or the like to prevent fog from forming. Such is because the plurality of spacer members (16) attach to the frame (12) at any number of points in order to provide much-needed spaces for air to circulate into the eye area. Accordingly, such spacer members (16) may be removably affixed to the frame top portion (12A), frame bottom portion (12B) or frame side portions (12C), as desired by the manufacturer or as per the activity in which the user is to be engaged. For instance, this ribbed-type configuration may allow for sufficient air circulation at all points of attachment of the protective device to the user, for a highly secure fit and maximum air circulation. Thus, unlike the prior art, the present invention is highly effective, yet requires no additional modification to the protective eyewear itself, reducing overall costs in the process.

Importantly, the spacer members (16) may comprise rounded or beveled edges in order to provide a comfortable fit against the user's forehead or upper facial area. In addition, as shown in FIG. 1A, the spacer members (16) may comprise angled or tapered edges (16A) in order to allow for additional air to flow into the eye area, as the edges (16A) create additional space between the members. Importantly, considering the type of eyewear upon which they are applied, the position of such spacer members may be either between the lenses and the frames or between the frames and the user's forehead.

Figure 1B:
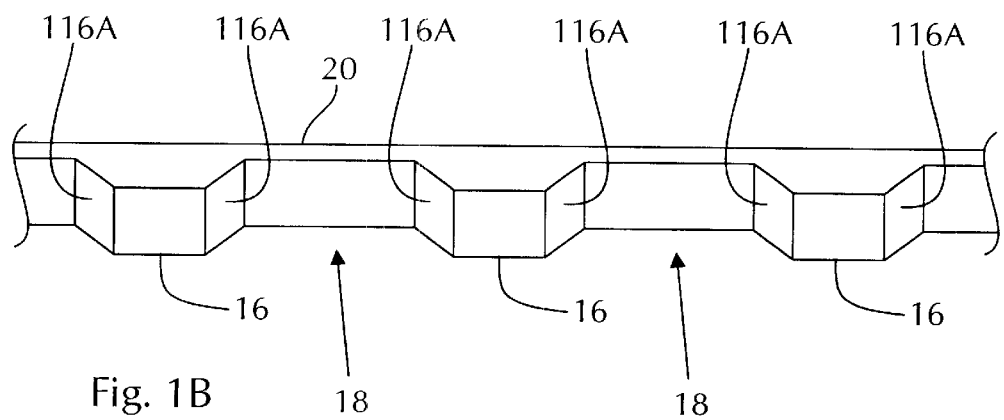
FIG. 1B is a front perspective view of several spacer members of the embodiment of the present invention illustrated in FIG. 1, further showing a removable strip comprising said spacer members.

Next, as an additional feature of the present invention, FIG. 1B is a front perspective view of several spacer members of the embodiment of the present invention illustrated in FIG. 1, further showing a removable strip comprising said spacer members. Illustrated are spacer members (16), spacer member side portions (16A), the cavity between spacer members (18), and removable strip (20). The removable strip (20) may be a separate, elongated and pliable member which is affixed to a previously-existing eyewear frame by a user or manufacturer in order to retrofit the prior item to enjoy the benefits of the concept of the present invention. As such, one can easily attach the spacer-containing strip to goggles or glasses via means such as simple adhesive or hook and loop fasteners.

Figure 2:
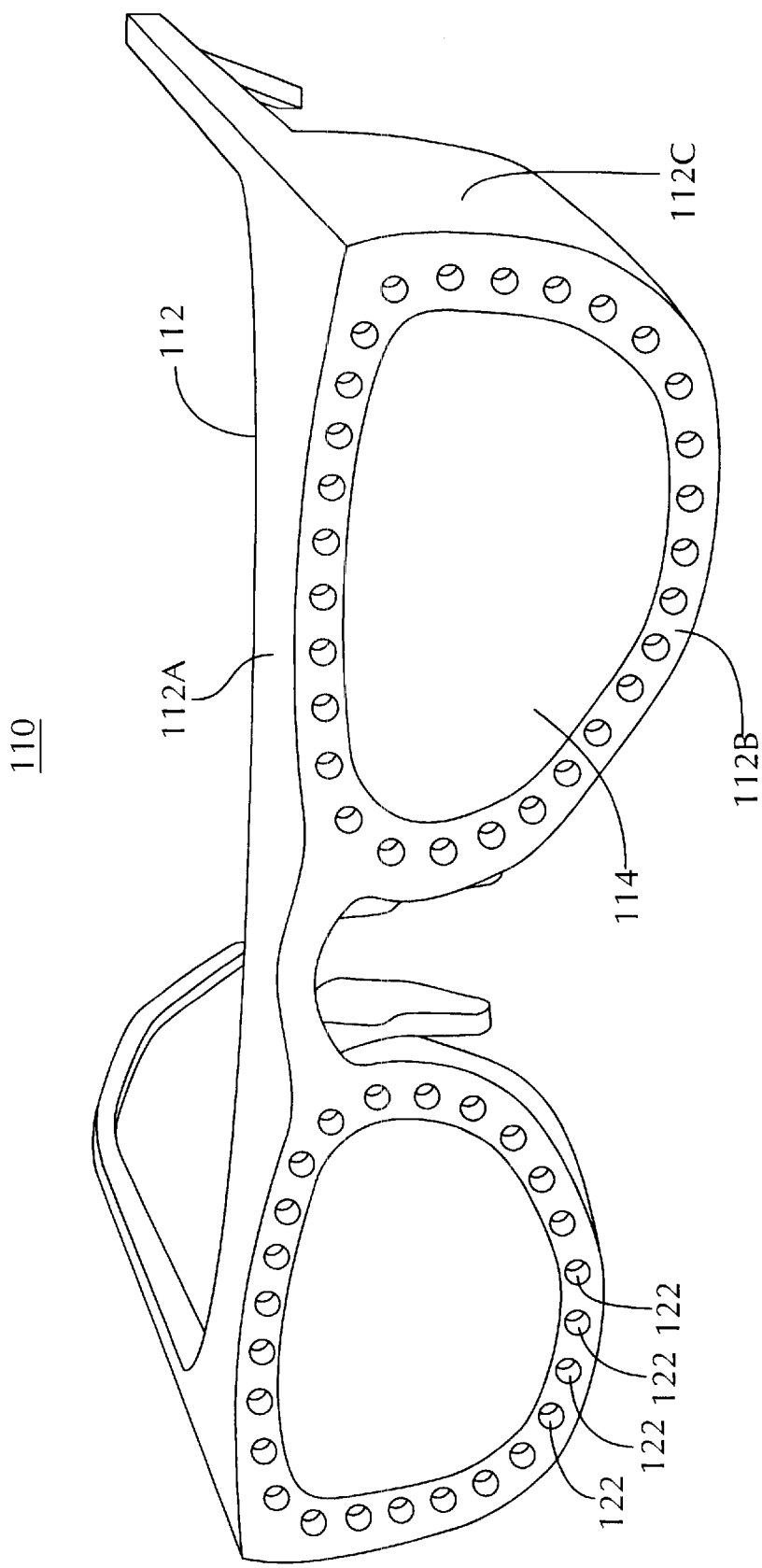
FIG. 2 is a front, three-quarter perspective view of a second embodiment of the present invention, illustrating the principal components utilized to mitigate formation of fog.

Regarding an additional mode of manufacture and usage, FIG. 2 is a front, three-quarter perspective view of a second embodiment of the present invention, illustrating the principal components utilized to mitigate formation of fog. Illustrated in the alternate embodiment (110) are the eyewear frame (112), frame top portion (112A), frame bottom portion (112B), frame side portion (112C), and apertures (122).

For the purposes of versatility, the additional embodiment of the present invention teaches the usage of air flow apertures—either in lieu of or in addition to aforementioned spacer members—in order to provide sufficient air circulation to the eye area to prevent condensation buildup and fog. As such, this embodiment is especially effective for activities in which the user is in forward motion, as the same would assist in air circulation needed to accomplish the purposes of the present invention.

Considering the foregoing, it is important to note that the apertures of the present invention may be tailored in size and diameter to the type of sport or activity in which the user is engaged. Thus, smaller apertures or smaller cavities between spacer members may be utilized on eyewear designed for fast-moving activities, while larger apertures or larger cavities between spacer members may be utilized on eyewear designed for slow-moving or more stationary activities.

In fact, one especially good example for either of the above embodiments lies in the sport of skiing. In this case, the cavities between the spacer members or air flow apertures may be just large enough to allow sufficient air to enter the mostly enclosed area, in consideration of the substantial speeds at which the user may travel. Not to be taken lightly in this regard is that fact that fog will form especially easily in skiing, given the difference between the "outside" temperature and "inside" goggle temperature closest to a perspiring user. Therefore, using the design of the present invention, the user will remain comfortable while enjoying the benefits of the fog-resistant construction.

Accordingly, the present invention will also be highly useful in other activities involving cold weather or temperature differential, such as bobsledding, luge, and ice hockey. In the case of ice hockey, a sufficient quantity of spacers may be located around the edge of the helmet where the visor portion or lens assembly is attached, in order to allow air to enter the area immediately above the user's nose and eyes.

Moreover, an additional example for usage of the present invention is the field of motorcycling and similar vehicles, wherein the speed at which the user is traveling necessitates smaller cavities between spacer members or smaller air flow apertures, depending upon which embodiment is utilized.

Finally, it should be noted that the concept of the present invention is even effective for surgeons' face masks, wherein the same greatly mitigates the incidence of fog during highly important activities when clear vision is imperative.

With regards to all descriptions and graphics, while the invention has been illustrated and described as embodied, it is not intended to be limited to the details shown, since it will be understood that various omissions, modifications, substitutions and changes in the forms and details of the device illustrated and in its operation can be made by those skilled in the art without departing in any way from the spirit of the invention.

Without further analysis, the foregoing will so fully reveal the gist of the present invention that others can readily adapt it for various applications without omitting features that, from the standpoint of prior art, constitute essential characteristics of the generic or specific aspects of this invention. What is claimed as new and desired to be protected by letters patent is set forth in the appended claims.

What is claimed is:

1. An improved fog-free protective eyewear apparatus comprising:
   a frame (12), comprising a frame top portion (12A), frame bottom portion (12B), and frame side portion (12C),
   at least one lens (14) contained within the frame,
   a plurality of generally soft, pliable spacer members (16) removably affixed to the frame along an entire periphery of an interior edge thereof, the spacer members comprising at least one polymer material with retention memory characteristics, functioning to allow the spacer members to de-form upon receiving a force thereto and subsequently return to their original structure and thickness; edges of the spacer members rounded to eliminate user discomfort, and the spacer members tapered with angled sides for increased air flow;
   the presence of such spacer members forming cavities between the spacer members (18), the spacer members functioning to come in contact with a user's face and encircle each eye of the user, thus functioning to separate the frame from the user's face, thus allowing air circulation from outside the eyewear to enter an area in front of the user's face to prevent fog from forming on the lenses and frame.

2. The fog-free protective eyewear apparatus as described in claim 1, wherein the spacer members are rigidly affixed to an elongated strip, the elongated strip removably affixed to the interior edge of the frame, functioning to allow the strip and spacer members to affix to previously existing eyewear frames.

3. The fog-free protective eyewear apparatus as described in claim 1, wherein the apparatus comprises indicia thereon.

4. The fog-free protective eyewear apparatus as described in claim 1, wherein the spacer members are manufactured in a variety of previously determined sizes and shapes, functioning to render the spacer members effective for multiple previously determined sporting events and hazardous activities.

5. The fog-free protective eyewear apparatus as described in claim 1, wherein the spacer members are removably affixed to the frame through usage of hook and loop fasteners.

6. The fog-free protective eyewear apparatus as described in claim 1, wherein the spacer members are retrofitted to previously-existing eyewear products.

7. The fog-free protective eyewear apparatus as described in claim 1, wherein the spacer members are retrofitted to previously-existing items selected from the group consisting of protective glasses, goggles, non-protective glasses, visors, helmets, and surgeons' masks.

8. The fog-free protective eyewear apparatus as described in claim 1, wherein the improved eyewear apparatus is utilized for activities selected from the group consisting of tennis, racquetball, football, hockey, skiing, snowmobiling, cycling, motorcycling, automobile racing, construction, woodworking, welding, landscaping, police usage, firefighting usage, medical usage, and military usage.

9. The fog-free protective eyewear apparatus as described in claim 1, wherein the spacer members attach to the equipment without modification to the equipment.

10. The fog-free protective eyewear apparatus as described in claim 1, wherein the spacer members are manufactured in a variety of previously determined colors and designs, functioning to match a decor of equipment upon which the spacer members are utilized.

11. The fog-free protective eyewear apparatus as described in claim 1, wherein the air flow cavities between spacer members vary in size according to the type of activity in which the apparatus is utilized.

12. The fog-free protective eyewear apparatus as described in claim 1, wherein the spacer members are of a generally similar width as an outside frame of the eyewear apparatus.

13. The fog-free protective eyewear apparatus as described in claim 1, wherein the spacer members attached to frames through usage of adhesives.

14. An improved fog-free protective eyewear apparatus comprising:

a frame (12), comprising a frame top portion (12A), frame bottom portion (12B), and frame side portion (12C), at least one lens (14) contained within the frame, a plurality of air flow apertures upon the frame along the entire periphery thereof, the presence of such air flow apertures functioning to allow air circulation from outside the eyewear to enter an area in front of the user's face to prevent fog from forming on the lenses and frame; and a plurality of padded spacer members affixed to an interior edge of the frame and a plurality of air flow apertures.

15. The fog-free protective eyewear apparatus as described in claim 14, wherein diameter of the apertures is of a range of one-sixteenth to three-eighths inches.

* * * * *